| (12) | United States Patent | (10) Patent No.: | US 7,540,613 B2 |
|---|---|---|---|
| | Severns | (45) Date of Patent: | Jun. 2, 2009 |

(54) DEVICE TO MONITOR RETINAL ISCHEMIA

(76) Inventor: Matthew L. Severns, 10549 Saint Paul St., Kensington, MD (US) 20895

( * ) Notice: Subject to any disclaimer, the term of this patent is extended or adjusted under 35 U.S.C. 154(b) by 174 days.

(21) Appl. No.: 11/507,248

(22) Filed: Aug. 19, 2006

(65) Prior Publication Data

US 2008/0058655 A1  Mar. 6, 2008

(51) Int. Cl.
*A61B 3/10* (2006.01)
*A61B 3/00* (2006.01)

(52) U.S. Cl. .................. 351/205; 351/200; 351/220; 351/221

(58) Field of Classification Search .................. 351/205, 351/200, 220, 221
See application file for complete search history.

(56) References Cited

U.S. PATENT DOCUMENTS

| 4,181,407 | A | 1/1980 | Razran |
|---|---|---|---|
| 4,846,567 | A | 7/1989 | Sutter |
| 4,877,322 | A | 10/1989 | Hill |
| 5,772,298 | A | 6/1998 | Miyake |
| 6,022,109 | A | 2/2000 | Dal Santo |
| 7,001,020 | B2 | 2/2006 | Yancey et al. |
| 2002/0024633 | A1* | 2/2002 | Kim et al. ............ 351/206 |
| 2004/0085514 | A1 | 5/2004 | Fransen |
| 2005/0254008 | A1* | 11/2005 | Ferguson et al. ............ 351/205 |

OTHER PUBLICATIONS

Bresnick, Korth, Groo and Palta; Archives of Ophthalmology 102:1307-11, 1984; electroretinographic oscillatory potentials predict progression of diabetic retinopathy.
Bresnick, Palta: Archives of Ophthalmology 105:660-4; 1987; Temporal aspects of the electroretinogram in diabetic retinopathy.
Bresnick, Palta; Archives of Ophthalmology 105:929-33, 1987; relation to severity of diabetic retinopathy.
Holopigian, Seiple, Lorenzo, Carr—Investigative Ophthalmology and Visual Science 33:2773-80, 1992: A comparison of photopic and scotopic electroretinographic changes in earl.

(Continued)

*Primary Examiner*—Jessica T Stultz
*Assistant Examiner*—Mahidere S Sahle
(74) *Attorney, Agent, or Firm*—Sean Wooden; Andrews Kurth LLP

(57) ABSTRACT

A battery powered, hand held device to determine of there is significant retinal ischemia in the eye of a patient. The device detects the consequences of impaired blood flow in the eye of the patient and has a light source for emitting a light and a diffuser or diffuse spheroidal reflector that redirects the light from the light source toward the patient's eye. A set of electrodes contact the patients skin proximate to the eye and receives an electrical signal representing the eye's electrical response to the light stimulus. A microcontroller interprets the electrical signal sensed by the electrodes by using an algorithm to determine the degree of retinal ischemia of the patient. In one embodiment, there is a control that establishes the intensity of the light stimulus by measuring and using the area of the pupil.

36 Claims, 2 Drawing Sheets

OTHER PUBLICATIONS

Johnson, Marcus, Elman, McPhee, Archives of Ophthalmology 106:348-52, 1988; Neovascularization in central retinal vein occlusion; electroretinographic findings.

Breton, Quinn, Keene, Dahmen and Brucker, Ophthalmology 96:1343-52, 1989, Electroretinogram parameters at presentation as predictors.

Severns, Johnson, Archives of Ophthallmology 111:1123-1130, 1993, Predicting outcome in Central Retinal Vein Occlusion Using the Flicker.

Severns, Johnson, Merritt, Applied OPtics 30:2106-2112, 1991. Automated estimation of implicit time and amplitude from the Flicker.

Severns, Johnson, Optical Society of America, pp. 10-13, 1991. Automated implicit time and amplitude determination for the 30Hz flicker electroretinogram.

Saladin, Investigative Ophthalmology and Visual Science 17:702-705, 1978. Television pupillometry via digital time processing.

Ephios AB, "Global Scan", Weblabs Marketing Solutions, weblabs.se.

* cited by examiner

DEVICE TO MONITOR RETINAL ISCHEMIA

FIELD OF THE INVENTION

The present invention relates to a device for monitoring retinal ischemia and, more particularly, to a hand held device that can easily determine if the eye of a patient is receiving sufficient blood flow.

BACKGROUND OF THE INVENTION

Diabetic retinopathy is a disease caused by progressively impaired blood flow to the retina of the eye. This impaired blood flow eventually leads to oxygen deprivation, or ischemia of the retina. Over time, the ischemia worsens and the retina begins to secrete hormones to produce new blood vessels. These blood vessels are very fragile and grow in inappropriate parts of the eye. They can rupture leading to blindness. Other conditions caused by worsening ischemia in the diabetic eye include macular edema, where the central part of the eye responsible for good vision develops a fluid bubble leading to poor central vision.

The progress of the disease can today be detected by an ophthalmologist, and when the disease is severe enough, it can be treated by burning the retina repeatedly with a laser (panretinal photocoagulation) which stops the secretion of angiogenic hormones (or inhibits their action). There are also drug therapy interventions available and under development that may delay the onset of inappropriate blood vessel development.

Accordingly, early detection of diabetic retinopathy would allow intervention at an earlier stage of the disease allowing better quality of life for diabetics whose vision could be preserved for a longer period of time. The American Academy of Ophthalmology recommends that diabetics that have had the condition for more than ten years get an eye examination annually. Despite the availability of diagnosis and treatment, diabetic retinopathy is the leading cause of blindness in working-age Americans, and is one of the leading causes of blindness worldwide.

At the present, ophthalmologists rely on two primary diagnostic tests for assessment of diabetic retinopathy.
1. Fundus photography is the practice of taking careful photographs of the back of the eye and grading them for the presence of certain characteristics. The photographs are typically taken by a highly trained technician using a specialized camera called a fundus camera. The grading of the photographs is performed either by an ophthalmologist or by specially trained "graders".
2. Fluorescein angiography involves injecting a fluorescent dye into the patient's vein and photographing the time course of the dye passing through the eye using a specialized camera system. This technique allows the assessment of blood flow across the surface of the eye, and allows an assessment of leakage from the blood vessels. Fluorescein angiography is performed by ophthalmologists or certified technicians and the interpretation of the photographs is performed either by an ophthalmologist or by specially trained "graders".

Diabetic retinopathy is not the only disease to cause damage to the eye through the mechanism of retinal ischemia. Less prevalent diseases, including central retinal vein occlusion (CRVO), central retinal artery occlusion (CRAO) and sickle cell anemia may also induce retinal ischemia leading to the growth of inappropriate new blood vessels in the eye.

It has been known for some time that features of the clinical electroretinogram (ERG) are strongly correlated with retinal ischemia and with the extent and severity of diabetic retinopathy. There are many reports in the academic literature describing the relationship between features of the ERG and severity of several types of retinal ischemia. Some of the articles include the following: Bresnick, G, Korth, K, Groo, A. and Palta, M. Archives of Ophthalmology 102: 1307-11 (1984) *Electroretinographic oscillatory potentials predict progression of diabetic retinopathy*; Bresnick, G. and Palta, M, Archives of Ophthalmology 105:60-664 (1987) *Temporal aspects of the electroretinogram in diabetic retinopathy*, and Bresnick, G and Palta, M, Archives of Ophthalmology 105: 929-33 (1987) *Oscillatory potential amplitudes, Relation to severity of diabetic retinopathy*.

Normally the ERG is recorded using a large instrument in a darkened room with electrodes placed directly onto the eye. Dilating drops are used to enlarge the pupil and anesthetic drops are used to numb the eye before placing the electrodes onto the eye. The waveforms are collected by a skilled technician and are usually interpreted by an ophthalmologist or PhD expert in visual electrophysiology. The aforedescribed disadvantages of the ERG have prevented its widespread use in assessing retinal ischemia.

As can therefore be seen, the present systems and methods of detecting retinal ischemia are by fundus photography, fluorescein angiography or by using a conventional ERG system. All of such methods require expensive equipment and facilities as well as highly trained personnel to operate and interpret the results.

Accordingly, it would, therefore, be desirable to have an inexpensive, hand held device that would be easy to operate, require little or no training to operate and interpret the results. It would be further advantageous to have such a device that could be used by general practice physicians to assess the health of diabetic eyes and thus significantly improve the number of diabetic eyes that are screened for retinopathy.

BRIEF SUMMARY OF THE INVENTION

Accordingly, the present invention relates to a compact, handheld electroretinographic monitoring device to assess retinal ischemia in the eyes of patients with diabetes or other ischemic eye diseases.

The present monitoring device can be manually placed in contact with the skin in proximity to the subject's eye and has a light source that emits a flash of light into the eye. The light is provided by a high intensity light emitting diode and that light is directed toward the eye by a diffuse spheroidal reflector to provide a uniform light into the eye. A return signal is received from the eye in response to the light stimulus and is detected by electrodes that contact the skin proximate to the eye. In an exemplary embodiment, there are three electrodes; a side electrode and two other electrodes oriented vertically with respect to the side electrode. The received signal is detected by the side electrode and one of the other electrodes.

In an exemplary embodiment, the electrodes are located in an electrode holder that is rotatably mounted to a hand held portion of the monitoring device and the electrode holder can be rotated with respect to the hand held portion in order to accommodate the difference in the anatomy of both the left and the right eyes of the subject. There can also be a system to determine which eye is being tested by measuring the impedance between the side electrode and each of the other electrodes or by determining the rotational orientation of the electrode holder with respect to the hand held portion.

There is an electrical circuit that controls the light directed toward the eye and measures the electrical signal the eye produces in response to the light. The time span between the flash of light and the time of the peak of the return signal is indicative of the degree of retinal ischemia of the patient.

The monitoring device is self-contained, that is, there is battery power provided, controls located in the hand held device and an electronic readout for the user. In an embodiment, there is a detector that determines the area of diameter of the pupil of the eye and determines the intensity of the light flash in accordance with that area or diameter. The detector can be a video camera.

As a further feature, the detector includes a source of illumination to illuminate the pupil and which is preferably a source of infrared radiation.

These and other features and advantages of the present invention will become more readily apparent during the following detailed description taken in conjunction with the drawings herein.

DETAILED DESCRIPTION OF THE INVENTION

Figure 1:
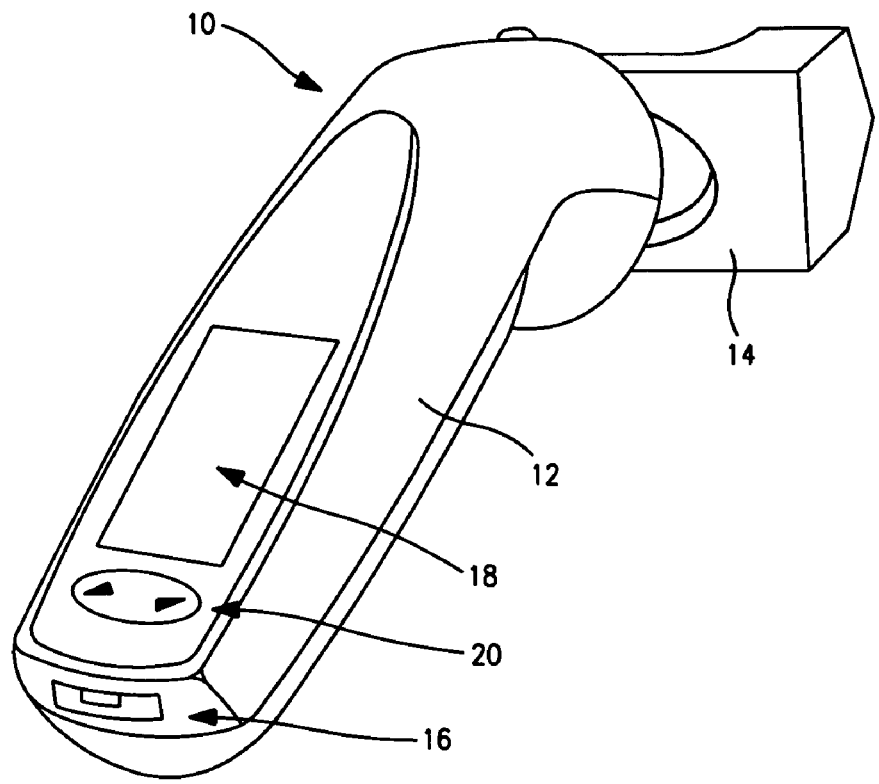
FIG. 1 is a perspective view of the hand held device of the present invention.

Referring now to FIG. 1, there is shown a hand held retinal ischemia monitoring device 10 of the present invention. As can be seen, the monitoring device 10 comprises a hand held portion 12 with an electrode holder 14 at its forward end that has electrodes (not shown in FIG. 1) that are adapted to be placed in contact with the skin of the patient proximate to either eye of the patient when the monitoring device 10 is in its operative position. As will be seen, the electrode holder 14 is preferably rotatably mounted to the hand held portion 12. The monitoring device 10 can have a battery compartment 16 to house the batteries to power its operation. In addition, there is a readout 18, as well as various controls 20, the use of which will be later explained.

Figure 2:
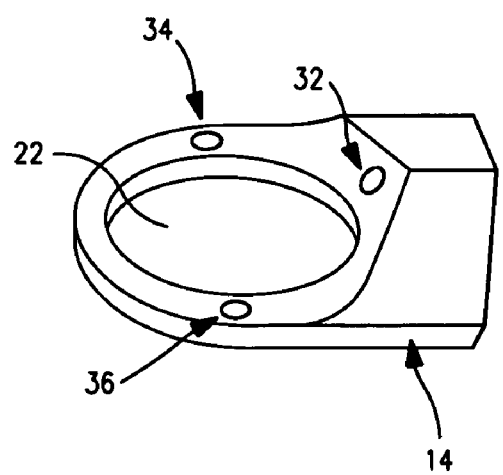
FIG. 2 is a perspective view of the electrode holder which is part of the hand held device of FIG. 1.

Turning now to FIG. 2, there is shown a perspective view of the electrode holder 14 of the present device. In the exemplary embodiment, the electrode holder 14 has a centrally located opening 22 and there are three electrodes; a side electrode 32 and two other electrodes 34, 36 that are located vertically away from the side electrode 32, and generally equidistant from the side electrode 32. The spacing of the electrodes 32, 34 and 36 is designed such that, when the hand held monitoring device 10 is placed against the skin of the patient proximate to the eye, the side electrode 32 is oriented at the side of the eye and one of the other two electrodes 34, 36 is in contact with the skin next to the lower lid of the eye. The remaining electrode is not touching the patient. Determination of which electrodes are in contact with the patient is made by measuring the impedance of the electrode pairs and allows the system to automatically establish the eye being tested.

The electrode holder 14 can be rotated 180 degrees with respect to the hand held portion 12 to adjust the orientation of the electrodes 32, 34 and 36 for left and right eyes and that rotation can also be sensed in order to determine which eye is being tested.

In the embodiment illustrated, the electrodes are combined as integral components of the hand held device 10, however, as an alternative embodiment, the electrodes can be disposable so that they are intended for one patient use and thus are readily attachable and detachable from the hand held portion 12 of the hand held monitoring device 10. As such, the only part of the hand held monitoring device 10 that actually contacts the patient would not need to be disinfected after each patient. With that embodiment, the electrodes can be embedded in a disposable plastic sheet so that a new electrode set is used for each test, thereby ensuring maximum protection against any infection passing from patient to patient.

While three electrodes 32, 34 and 36 are illustrated in FIG. 2, there can be a lesser number of electrodes that can be used to still effectively carry out the present invention. As will later be seen, the use of three electrodes has other advantages that are gained in the use of the hand held monitoring device 10.

Figure 3:
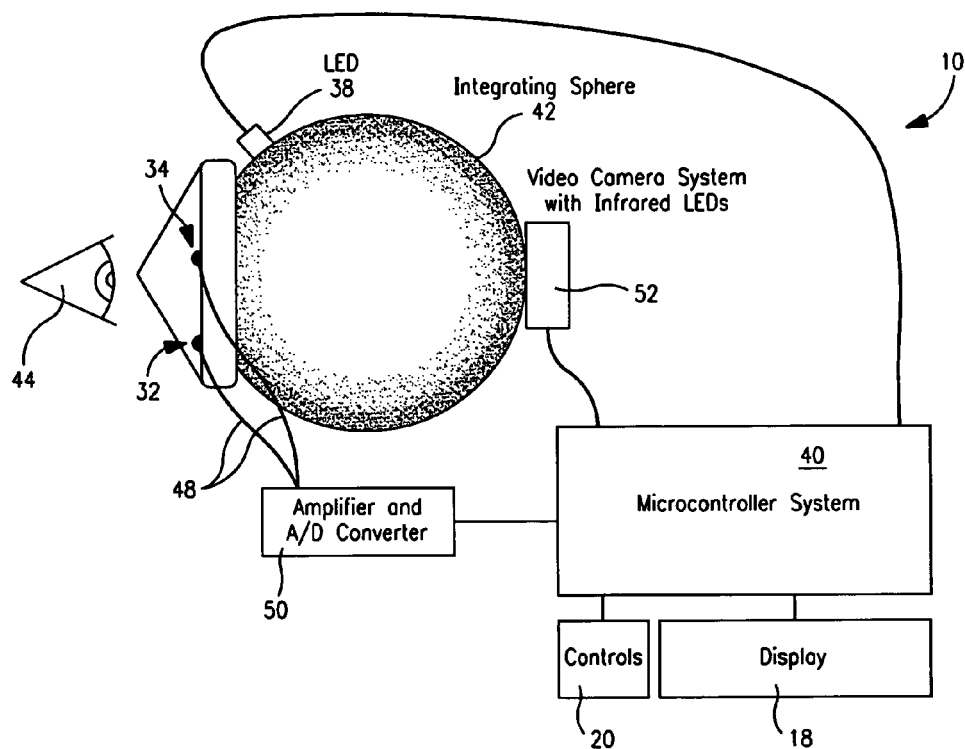
FIG. 3 is schematic view of the present invention.

Turning now to FIG. 3, taken along with FIG. 1, there is shown a schematic view of the present invention to illustrate the components that are contained within the hand held monitoring device 10 of FIG. 1. A light source 38 is used to provide a light stimulus to the eye and the light source 38 can be a light emitting diode, (LED) that is compact and therefore suitable for a portable device as opposed to the prior art xenon flashtube or array of LED's. The current high brightness LED's have sufficient brightness for carrying out the present invention with an efficient diffuser, however, it may be that for some applications a plurality of LEDs may be used to make up the light source 38.

The light source is 38 controlled by a microcontroller 40 that, as will be seen, provides the overall control of the hand held monitoring device 10 but is sufficiently small so as to readily fit into the hand held monitoring device 10. The light source 38 is positioned so as to protrude inwardly of a diffuse spheroidal reflector 42 so that the light from the light source is directed uniformly toward the eye 44 from all directions. In the illustrated embodiment, the diffuse spheroidal reflector 42 is spheroidal in configuration with the interior surface coated white to enhance the reflectivity. The use of the diffuse spheroidal reflector 42 provides an even illumination to most of the retina of the eye 44.

As stated, the control of the light source 38 is by means of the microcontroller 40 which not only controls the timing of the firing of the LED, but also the intensity thereof. The control of the intensity of the light source 38 will be later explained. As to the timing, the LED provides a series of brief flashes of light spaced about every 30 milliseconds, however, other stimulus waveforms or stimulus frequencies can also be utilized.

In a preferred embodiment, the intensity of the LED or light source 38 is also modulated to produce a constant background illumination. That background illumination allows the eye 44 to be brought to a known state of light adaptation, which is important for a consistent response as will be later be understood.

Figure 4:
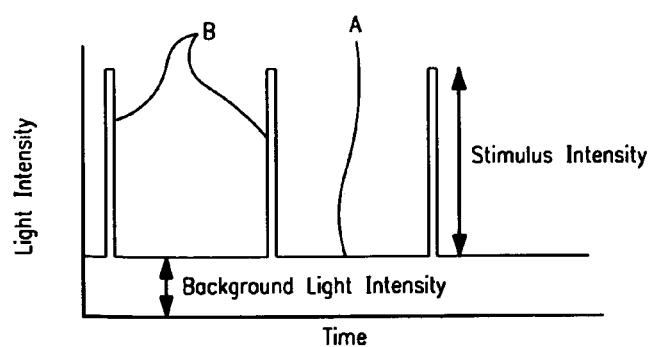
FIG. 4 is a graph showing light intensities of the background light and stimulus light used with the present invention.

Turning briefly, therefore to FIG. 4, there is a graph plotting time vs. light intensity illustrating the light intensity of the background illumination, identified as A as well as the intensity of the brief flashes of light identified as B. As can be seen, the background illumination intensity is established and maintained whereas the brief flashes of light are of a high intensity and short duration.

Returning to FIG. 3, as previously explained, the light stimulus by the light source 38 gives rise to an electrical signal from the eye 44 that is sensed by the electrodes 32, 34 for example (it could be electrodes 32, 36) contacting the skin of the patient proximate to the eye 44 and the electrical signal is communicated by wires 48 to an amplifier and A/D converter shown as block 50. The amplifier is preferably a biomedical amplifier using 24 bit analog to digital converters that eliminates gain adjustment and the prolonged recovery from saturation of conventional amplifiers.

Typically, conventional amplifiers have required some oversight by a technician during testing to assure that the gain setting was correctly matched to the input range of the analog to digital converter. Further, such conventional amplifiers could saturate (fail to respond to the input signal) and might take tens of seconds to recover the ability to respond to a signal. The saturation is difficult to distinguish from a lack of response from the patient making reliable automation of signal acquisition difficult.

To avoid the problems, in a preferred embodiment, the system used a low gain differential amplifier (no more than 32x) and a high resolution (typically 24 bit) differential analog to digital converter to acquire the signal from the eye 44 by means of the skin electrodes 32, 34. Thus, the amplifier has a very high tolerance for noise and offsets, while producing highly faithful reproduction of the input waveform. The amplifier and A/D converter of block 50 are also immune to prolonged saturation caused by interfering signals. Input impedance of the system is very high (>10 MΩ) so that the relatively high impedance of the electrodes 32, 34 contacting the skin does not affect the results. The output of the analog to digital converter in block 50 is connected to the microcontroller 40, which analyzes the data.

A further feature of the present hand held monitoring device 10 is that there is a system to determine which eye 44 is being tested by the device i.e the right eye or the left eye. Returning briefly to FIG. 2, in that exemplary embodiment, there are three electrodes 32, 34 and 36 that are formed in the configuration of a triangle with one electrode 32 along the side of the eye 44 with the other two electrodes 34, 36 located vertically offset with respect to the side electrode 32. Thus the system to determine which eye is being tested provides a low current source between pairs of electrodes to measure the electrode impedance. The current is used to determine the particular eye being tested and is switched off during the testing itself and only the two electrodes determined to be touching the skin are used to carry out the testing procedure. Accordingly, the testing will be carried out using the side electrode 32 and either one of the other two electrodes 34 or 36.

As a further feature of the present invention, and which may be optional, there is a system to establish the intensity of the light source 38 based upon the area of the pupil of the eye 44 so that the light stimulus to the retina will be constant among the various patients without the need for dilating drops to be placed in the eye to widen the pupil. Accordingly the system comprises a video camera 52 that is positioned so as to view the pupil of the eye 44 and measure the area of the pupil. The video camera 52 can be a small, relatively low resolution (e.g. 320-240 pixel) device having an illumination source to illuminate the pupil for the video camera 52.

The illumination source for the pupil measurement system is preferably one or more infrared LED's that are located nearly coaxial with the lens of the video camera 52 to so that the reflected light from the interior of the eye 44 creates a highly visible pupil to the video camera 52. With the use of infrared light radiation the light is not visible to the eye but does provide sufficient illumination for the video camera 52. As such, the area of the pupil can be readily determined through a simple thresholding and pixel counting algorithm. There are several system for measuring the pupil area that are published in the art and one is shown and described in Investigative Ophthalmology and Visual Science, 17:702-705 (1978) by Salidin, J J and entitled *Television Pupillometry via digital time processing*.

In any event, the area of the pupil can be determined by the microcontroller 40 so that the intensity of the light source 38 is established based on that pupil area such that the light stimulus is basically the same for each patient and for successive tests with same patient. The system can also be used to determine if the eye is shut, for example, in the event of a blink, and eliminate that part of the signal from the analysis.

The analysis of the data from the electrical signals sensed by the electrodes 32, 34 is, as described, carried out by the microcontroller 40. The algorithms for specifically assessing retinal ischemia in a patient have been published. See, for example, Applied Optics 30:2106-2112 (1991) by Severns, M L, Johnson, M A and Merritt, S A *Automated estimate of implicit time and amplitude of the flicker electroretinogram* and 1991 Technical Digest Series, Washington, D.C; Optical Society of America, pp. 10-13 (1991) by Severns, M L and Johnson, M A *Automated implicit time and amplitude determination for the 30 Hz flicker electroretinogram: performance prediction of neovascularization central retinal vein occlusion*.

In an exemplary embodiment, the signals from the skin electrodes 32, 34 are analyzed for the amount of noise present to determine if accurate and clinically meaningful measurements can be made. If the signal to noise ratio is marginal, additional data can be collected to improve the estimate. Next, a sine wave is fit to the data to determine the amount of elapsed time between the actuation of the stimulus and the maximal response of the eye. This measurement has been shown to be a highly sensitive measure of the extent of ischemia in the eye. See the Applied Optics publication previously cited.

As further components of the present hand held monitoring device 10, (FIG. 1) there are controls 20 that can be used to initiate each test and to enter customized settings. In addition, the readout 18 provides a visual readout to the user of the results of each test, that is, the readout 18 provides a visual readout to the user that is related to the amount of retinal ischemia of the eye.

Accordingly, the operation of the hand held device 10 can now be summarized, using FIGS. 1-4. The electrode holder 14 is adjusted for the eye to be tested by rotating it to the appropriate orientation. The hand held device 10 is held against the patient proximate to the eye of the patient such that at least two of the skin electrodes 32 and 34 or 32 and 36 contact the skin of the patient. The hand held monitoring device 10 is initialized by pressing a button on the device by means of the controls 20. The battery power is thus engaged to power the microcontroller 40 that energizes the light source 38 to provide a continual adapting or background light of a predetermined, relatively low intensity for a period of about 1 minute.

Next, the microcontroller 40 determines which eye is being tested by determining the impedance between the side electrode and each of the other electrodes. Once the identification of the eye has been determined, the impedance measurement is discontinued. Alternatively, the eye being tested can be determined by sensing the rotational orientation of the electrode holder 14 relative to the hand held portion 12

The microcontroller 40 then commences the flashing of the light source 38 at about 30 Hz to stimulate the retina. At the same time, the video camera 52 measures the area of the pupil and the microcontroller 40 adjusts the intensity of the light source 38 in accordance with that area. As indicated, that feature may not be used with every application of the device 10. The microcontroller then receives the electrical signal produced by the eye from the skin electrodes 32, 34 and the electrical signal is fed into the microcontroller 40 for processing to determine, using known algorithms, the resulting electroretinogram and present the elapsed delay time between the light stimulus and the peak of the received electrical signal (or interpret the electroretinogram of the skin electrodes 32, 34) and an estimate of the reliability of the measurement on the readout 18.

In an alternative embodiment, the waveform data can be displayed on the readout 18 or downloaded to a reading unit for viewing by the physician. The data and results also may be printed out to be entered into the patient record as hard copy or electronically.

Those skilled in the art will readily recognize numerous adaptations and modifications which can be made to the hand held retinal ischemic monitoring device of the present invention which will result in an improved device an method of using the same, yet all of which will fall within the scope and spirit of the present invention as defined in the following claims. Accordingly, the invention is to be limited only by the following claims and their equivalents.

What is claimed is:

1. A hand held device to detect the effects of impaired blood flow in the eye of a subject, the device comprising:
    a light source for emitting a light,
    a light diffusing means adapted to receive the light from the light source and to redirect the light toward the eye of a subject, wherein the light diffusing means redirects the light to provide a substantially even illumination to the retina of the eye;
    means to provide the retina with substantially constant illumination from the light, regardless of the size of the pupil of the eye;
    at least one electrode adapted to contact the subject at a location proximate to the eye, the at least one electrode receiving an electrical signal from the eye of the subject responding to the stimulation by the light directed toward the eye, and
    an electronic circuit to control the light directed toward the eye of the subject and to measure the electrical signal received by the at least one electrode to determine whether blood flow is impaired within the eye of a subject.

2. The hand-held device of claim 1 wherein the light diffusing means is a diffuse spheroidal reflector.

3. The hand-held device of claim 1 wherein the light source is a light emitting diode.

4. The hand-held device of claim 1 wherein the electronic circuit measures the elapsed time between the time the light is directed toward the eye and the time the peak electrical signal is detected by the at least one electrode.

5. The hand-held device of claim 1 wherein the device includes batteries to power the light source and the electronic circuit.

6. The hand-held device of claim 1 wherein the means to provide the retina with substantially constant illumination includes a detector to determine the diameter or area of the pupil of an eye.

7. The hand-held device of claim 6 wherein the detector is a video camera.

8. The hand held device of claim 7 wherein the video camera includes an illumination device to illuminate the pupil for viewing by the video camera.

9. The hand held device of claim 8 wherein the illumination device is a source of infrared radiation.

10. The hand-held device of claim 6 wherein the means to provide the retina with substantially constant illumination further includes an electronic circuitry to establish the intensity of the light in accordance with the diameter or area of the pupil determined by the detector.

11. The hand-held device of claim 1 wherein at least one electrode comprises three electrodes.

12. The hand-held device of claim 11 wherein the device comprises a hand held portion and an electrode holder that is rotatably mounted to the hand held portion.

13. The hand-held device of claim 12 further including an electronic circuit to interrogate the electrodes or to sense their position relative to the hand held portion to determine whether the device is being positioned proximate to the right eye or the left eye of a subject.

14. The hand-held device of claim 11 wherein the electrical signal is received by one electrode positioned at the side of an eye and one of the other electrodes.

15. A method of determining whether the blood flow within the eye of a subject is impaired, the method comprising the steps of:
    providing a hand held device having a light source, a light diffuse reflector and at least one electrode,
    positioning the device such that the at least one electrode contacts the skin of the subject proximate the eye,
    activating the light source to direct light towards the eye of a subject, wherein the light automatically provides substantially even and constant illumination to the retina of the eye regardless of the size of the pupil of the eye,
    detecting an electrical signal by the at least one electrode responsive to the stimulation of the eye by the light, and
    determining whether blood flow within the eye is impaired by using a signal indicative of activating the light source and the electrical signal detected by the at least one electrode.

16. The method of claim 15 wherein the step of providing a hand held device comprises providing a hand held device having a light source comprising a light emitting diode.

17. The method of claim 15 wherein the step of providing a hand held device comprises providing a hand held device having three electrodes.

18. The method of claim 17 wherein the step of positioning the device comprises positioning the device such that one electrode contacts the subjects skin at the side of an eye and another electrode contacts the skin of the subject below the eye.

19. The method of claim 15 wherein the step of determining if the blood flow is impaired comprises measuring the time between the activation of the light source and the time the electrical signal is detected by the at least one electrode reaches its maximum value.

20. The method of claim 15 wherein the step of providing a hand held device comprises providing a hand held device having a diffuse spheroidal reflector.

21. A system for detecting the retinal ischemia of a patient comprising:
    a hand held device to detect impaired blood flow in the eye of a subject, the device comprising
        a light source for emitting a light,
        a reflector or diffuser adapted to receive the light from the light source and to redirect the light toward the eye of a subject, wherein the reflector or diffuser redirects the light, providing substantially even illumination to the retina of the eye;
        means to provide the retina with substantially constant illumination from the light, regardless of the size of the pupil of the eye;
        at least one electrode adapted to contact the subject at a location proximate to the eye, the at least one electrode receiving an electrical signal from the subject responding to the stimulation by the light directed toward the eye of the subject, an amplifier and an analog to digital converter to provide a digitized signal indicative of the electrical signal from the subject, and a microcontroller, the microcontroller activating the light source and adapted to receive the digitized signal from the subject from the at least one electrode, the microcontroller using the activation of the light source and the digitized signals to determine the retinal ischemia of a patient.

22. The system as defined in claim 21 wherein the amplifier is a low gain differential amplifier.

23. The system as defined in claim 21 wherein the microcontroller controls the intensity of the light source.

24. The system as defined in claim 23 wherein the means to provide the retina with substanially constant illumination includes a system to determine the area of the pupil of an eye and wherein the microcontroller controls the intensity of the light source based on the pupil area.

25. The system as defined in claim 21 wherein the light source emits brief light flashes and the microcontroller controls the frequency of activation of brief flashes of the light source.

26. The system as defined in claim 25 wherein the microcontroller controls the frequency of the brief flashes to be about every 30 milliseconds.

27. The system as defined in claim 24 wherein the system to determine the area of the pupil comprises a video camera having a source of illumination.

28. The system as defined in claim 27 wherein the source of illumination comprises an infrared light source.

29. The system as defined in claim 21 wherein the reflector or diffuser is a diffuse spheroidal reflector having a diffuse light reflecting surface.

30. The system as defined in claim 21 wherein the light source is at least one light emitting diode.

31. The hand held device of claim 1 wherein the means to provide the retina with substantially constant illumination includes an electronic circuit to control the light so as to automatically provide the substantially even and constant illumination to the retina of the eye regardless of the size of the pupil of the eye.

32. The system of claim 21 wherein the microcontroller controls the light source so as to automatically provide the substantially even and constant illumination to the retina of the eye regardless of the size of the pupil of the eye.

33. A hand held device to detect the effects of impaired blood flow in the eye of a subject, the device comprising:
   a light source for emitting a light,
   a light diffusing means adapted to receive the light from the light source and to redirect the light toward the eye of a subject, wherein the light diffusing means redirects the light, providing substantially even illumination to the retina of the eye;
   means to provide the retina with substantially constant illumination from the light, regardless of the size of the pupil of the eye; and
   at least one electrode adapted to contact the subject at a location proximate to the eye, the at least one electrode receiving an electrical signal from the eye of the subject responding to the stimulation by the light directed toward the eye, wherein the electrical signal contains information indicating whether the eye is deprived of oxygen.

34. A hand held device to measure diabetic retinopathy in the eye of a subject, the device comprising:
   a light source for emitting a light,
   a light diffusing means adapted to receive the light from the light source and to redirect the light toward the eye of a subject, wherein the light diffusing means redirects the light uniformly, providing substantially even illumination to the retina of the eye;
   means to provide the retina with substantially constant illumination from the light, regardless of the size of the pupil of the eye; and
   at least one electrode adapted to contact the subject at a location proximate to the eye, the at least one electrode receiving an electrical signal from the eye of the subject responding to the stimulation by the light directed toward the eye, wherein the electrical signal contains information indicating whether the eye is afflicted with diabetic retinopathy.

35. The hand held device of claim 34 further comprising a readout that provides a visual readout related to the severity of the diabetic retinopathy.

36. The hand held device of claim 34 further comprising a microcontroller programmed to analyze the electrical signal information to determine the severity of diabetic retinopathy in the eye.

* * * * *